United States Patent
Kim et al.

(10) Patent No.: US 9,474,510 B2
(45) Date of Patent: Oct. 25, 2016

(54) ULTRASOUND AND SYSTEM FOR FORMING AN ULTRASOUND IMAGE

(71) Applicant: SAMSUNG MEDISON CO., LTD., Gangwon-do (KR)

(72) Inventors: Deok Gon Kim, Seoul (KR); Min Woo Kim, Seoul (KR); Hyoung Jin Kim, Seoul (KR); Sung Hoo Hong, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 646 days.

(21) Appl. No.: 13/728,488

(22) Filed: Dec. 27, 2012

(65) Prior Publication Data
US 2013/0184586 A1 Jul. 18, 2013

(30) Foreign Application Priority Data
Dec. 27, 2011 (KR) .......... 10-2011-0143837

(51) Int. Cl.
*A61B 8/08* (2006.01)
*G01S 15/89* (2006.01)
*G01S 7/52* (2006.01)

(52) U.S. Cl.
CPC ......... *A61B 8/5207* (2013.01); *G01S 7/52085* (2013.01); *G01S 15/8979* (2013.01); *G01S 7/52034* (2013.01)

(58) Field of Classification Search
CPC ............. A61B 8/5207; G01S 7/52085; G01S 7/52034; G01S 15/8979
See application file for complete search history.

(56) References Cited

U.S. PATENT DOCUMENTS

| | | | |
|---|---|---|---|
| 5,487,389 A * | 1/1996 | Banjanin et al. | 600/455 |
| 5,833,613 A * | 11/1998 | Averkiou et al. | 600/440 |
| 5,961,462 A | 10/1999 | Loupas et al. | |
| 6,390,980 B1 * | 5/2002 | Peterson | G01S 15/8995 600/443 |
| 2007/0073152 A1 * | 3/2007 | Washburn | A61B 8/06 600/441 |
| 2007/0161898 A1 | 7/2007 | Hao et al. | |
| 2008/0009725 A1 | 1/2008 | Bae et al. | |
| 2008/0228078 A1 | 9/2008 | Kim et al. | |
| 2011/0295116 A1 * | 12/2011 | Lee | G01S 7/52088 600/437 |

FOREIGN PATENT DOCUMENTS

EP 2 392 945 A2 12/2011
KR 10-2007-0113084 A 11/2007
(Continued)

OTHER PUBLICATIONS

European Search Report issued in European Application No. 12199039.4-1812 dated Jul. 23, 2014.
Korean Office Action issued in KR Application No. 10-2011-0143837 mailed May 15, 2013.
(Continued)

*Primary Examiner* — Bo J Peng
(74) *Attorney, Agent, or Firm* — McDermott Will & Emery LLP

(57) ABSTRACT

An ultrasound system and a method of forming an ultrasound image by selectively extracting ultrasound data necessary for forming the ultrasound image from stored ultrasound data are disclosed. In one embodiment, an ultrasound system includes a storage unit configured to store ultrasound data acquired from an object; and a processor configured to selectively extract ultrasound data necessary for forming a target ultrasound image from the ultrasound data stored in the storage unit, and to form the target ultrasound image by using the extracted ultrasound data.

16 Claims, 19 Drawing Sheets

(56) References Cited

FOREIGN PATENT DOCUMENTS

| | | |
|---|---|---|
| KR | 10-2009-0069802 A | 7/2009 |
| KR | 10-0961854 B1 | 6/2010 |
| WO | 2006113445 A1 | 10/2006 |
| WO | 2009/158399 A1 | 12/2009 |

OTHER PUBLICATIONS

Korean Notice of Allowance, issued in Korean Application No. 10-2011-0143837, dated Mar. 14, 2014.
Korean Notice of Final Rejection, issued in Korean Applicatin No. 10-2011-0143837 dated Dec. 23, 2013.

\* cited by examiner

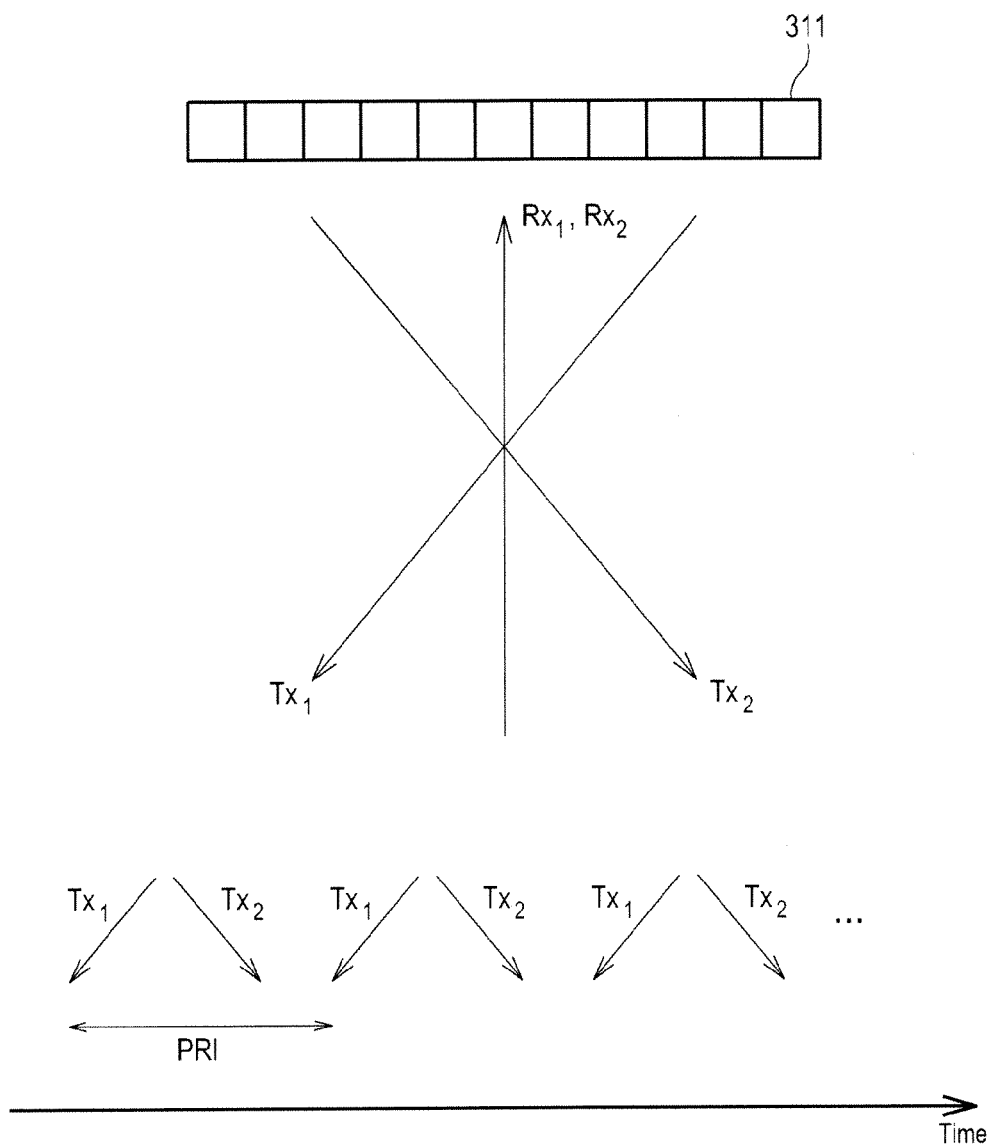

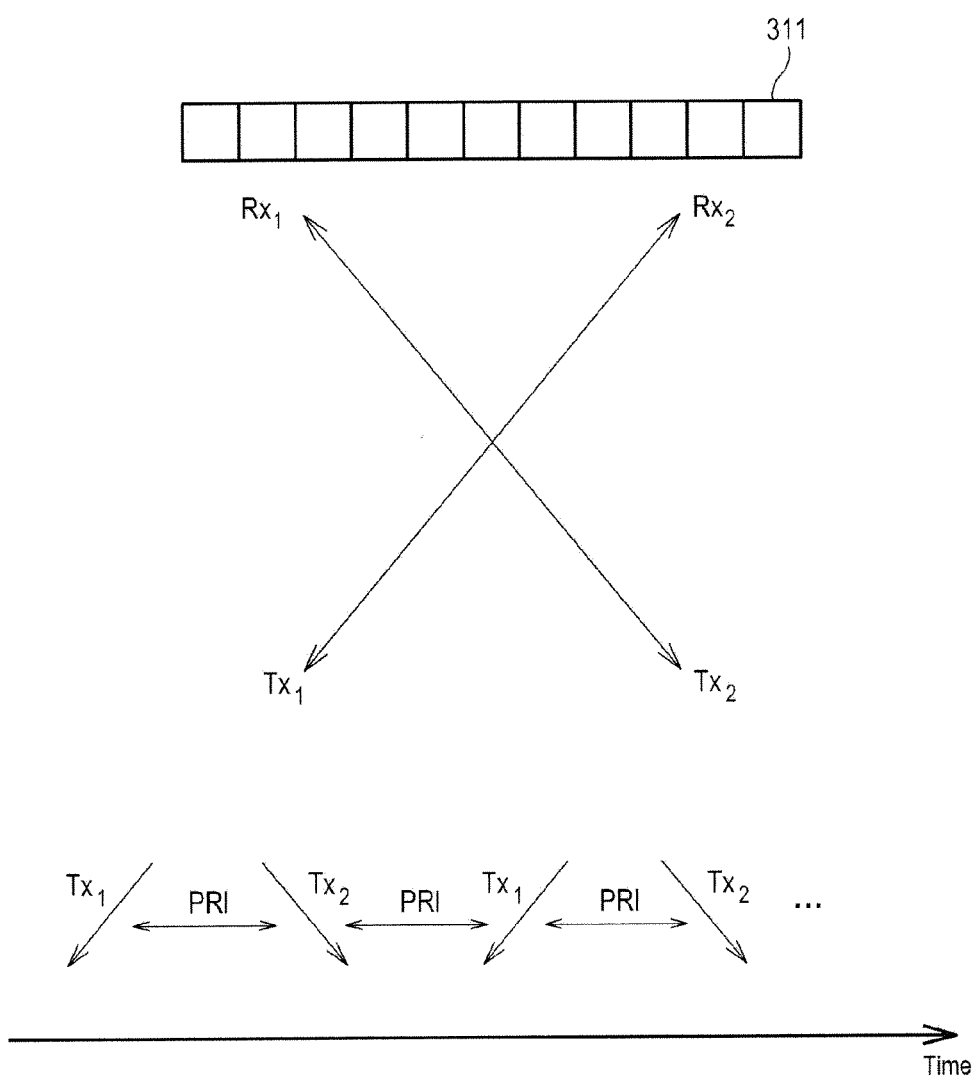

FIG. 7

| CH$_1$ | CH$_2$ | CH$_3$ | CH$_4$ | CH$_5$ | CH$_6$ | CH$_7$ | CH$_8$ | CH$_9$ | CH$_{10}$ | CH$_{11}$ | ... | CH$_p$ |
|---|---|---|---|---|---|---|---|---|---|---|---|---|
| S$_{1,1}$ | S$_{2,1}$ | S$_{3,1}$ | S$_{4,1}$ | S$_{5,1}$ | S$_{6,1}$ | S$_{7,1}$ | S$_{8,1}$ | S$_{9,1}$ | S$_{10,1}$ | S$_{11,1}$ | ... | S$_{p,1}$ |
| S$_{1,2}$ | S$_{2,2}$ | S$_{3,2}$ | S$_{4,2}$ | S$_{5,2}$ | S$_{6,2}$ | S$_{7,2}$ | S$_{8,2}$ | S$_{9,2}$ | S$_{10,2}$ | S$_{11,2}$ | ... | S$_{p,2}$ |
| S$_{1,3}$ | S$_{2,3}$ | S$_{3,3}$ | S$_{4,3}$ | S$_{5,3}$ | S$_{6,3}$ | S$_{7,3}$ | S$_{8,3}$ | S$_{9,3}$ | S$_{10,3}$ | S$_{11,3}$ | ... | S$_{p,3}$ |
| S$_{1,4}$ | S$_{2,4}$ | S$_{3,4}$ | S$_{4,4}$ | S$_{5,4}$ | S$_{6,4}$ | S$_{7,4}$ | S$_{8,4}$ | S$_{9,4}$ | S$_{10,4}$ | S$_{11,4}$ | ... | S$_{p,4}$ |
| S$_{1,5}$ | S$_{2,5}$ | S$_{3,5}$ | S$_{4,5}$ | S$_{5,5}$ | S$_{6,5}$ | S$_{7,5}$ | S$_{8,5}$ | S$_{9,5}$ | S$_{10,5}$ | S$_{11,5}$ | ... | S$_{p,5}$ |
| S$_{1,6}$ | S$_{2,6}$ | S$_{3,6}$ | S$_{4,6}$ | S$_{5,6}$ | S$_{6,6}$ | S$_{7,6}$ | S$_{8,6}$ | S$_{9,6}$ | S$_{10,6}$ | S$_{11,6}$ | ... | S$_{p,6}$ |
| ... | ... | ... | ... | ... | ... | ... | ... | ... | ... | ... | ... | ... |
| S$_{1,t}$ | S$_{2,t}$ | S$_{3,t}$ | S$_{4,t}$ | S$_{5,t}$ | S$_{6,t}$ | S$_{7,t}$ | S$_{8,t}$ | S$_{9,t}$ | S$_{10,t}$ | S$_{11,t}$ | ... | S$_{p,t}$ |

UI

| P$_{1,1}$ | P$_{1,2}$ | P$_{1,3}$ | P$_{1,4}$ | P$_{1,5}$ | P$_{1,6}$ | P$_{1,7}$ | P$_{1,8}$ | P$_{1,9}$ | ... | P$_{1,N}$ |
|---|---|---|---|---|---|---|---|---|---|---|
| P$_{2,1}$ | P$_{2,2}$ | P$_{2,3}$ | P$_{2,4}$ | P$_{2,5}$ | P$_{2,6}$ | P$_{2,7}$ | P$_{2,8}$ | P$_{2,9}$ | ... | P$_{2,N}$ |
| P$_{3,1}$ | P$_{3,2}$ | P$_{3,3}$ | P$_{3,4}$ | P$_{3,5}$ | P$_{3,6}$ | P$_{3,7}$ | P$_{3,8}$ | P$_{3,9}$ | ... | P$_{3,N}$ |
| P$_{4,1}$ | P$_{4,2}$ | P$_{4,3}$ | P$_{4,4}$ | P$_{4,5}$ | P$_{4,6}$ | P$_{4,7}$ | P$_{4,8}$ | P$_{4,9}$ | ... | P$_{4,N}$ |
| P$_{5,1}$ | P$_{5,2}$ | P$_{5,3}$ | P$_{5,4}$ | P$_{5,5}$ | P$_{5,6}$ | P$_{5,7}$ | P$_{5,8}$ | P$_{5,9}$ | ... | P$_{5,N}$ |
| P$_{6,1}$ | P$_{6,2}$ | P$_{6,3}$ | P$_{6,4}$ | P$_{6,5}$ | P$_{6,6}$ | P$_{6,7}$ | P$_{6,8}$ | P$_{6,9}$ | ... | P$_{6,N}$ |
| P$_{7,1}$ | P$_{7,2}$ | P$_{7,3}$ | P$_{7,4}$ | P$_{7,5}$ | P$_{7,6}$ | P$_{7,7}$ | P$_{7,8}$ | P$_{7,9}$ | ... | P$_{7,N}$ |
| ... | ... | ... | ... | ... | ... | ... | ... | ... | ... | ... |
| P$_{M,1}$ | P$_{M,2}$ | P$_{M,3}$ | P$_{M,4}$ | P$_{M,5}$ | P$_{M,6}$ | P$_{M,7}$ | P$_{M,8}$ | P$_{M,9}$ | ... | P$_{M,N}$ |

|   |   |   |   |   |   |   |   |   |   |   |
|---|---|---|---|---|---|---|---|---|---|---|
|   |   |   |   |   |   |   |   |   |   |   |
| $S_{6,4}$ |   |   |   |   |   |   |   |   |   |   |
| $S_{6,3}$ $S_{6,4}$ | $S_{6,3}$ $S_{6,4}$ |   |   |   |   |   |   |   | $S_{6,3}$ $S_{6,4}$ |   |
|   | $S_{6,3}$ $S_{6,4}$ | $S_{6,3}$ $S_{6,4}$ | $S_{6,3}$ $S_{6,4}$ | $S_{6,3}$ | $S_{6,3}$ | $S_{6,3}$ | $S_{6,3}$ $S_{6,4}$ | ... |   |   |
|   |   |   | $S_{6,4}$ | $S_{6,4}$ | $S_{6,4}$ | $S_{6,4}$ | $S_{6,4}$ | $S_{6,4}$ |   |   |
|   |   |   |   |   |   |   |   |   |   |   |
|   |   |   |   |   |   |   |   |   |   |   |
|   |   |   |   |   |   |   |   |   |   |   |
|   |   |   |   |   |   |   |   |   |   |   |

— UI

FIG. 12
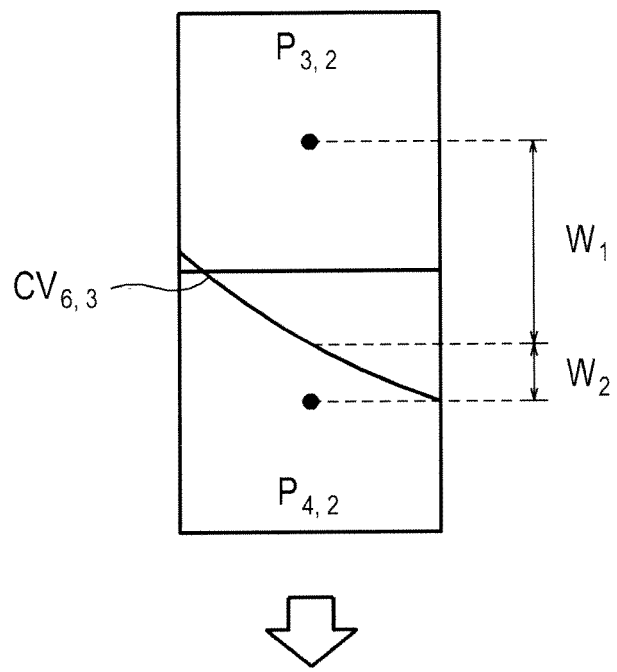
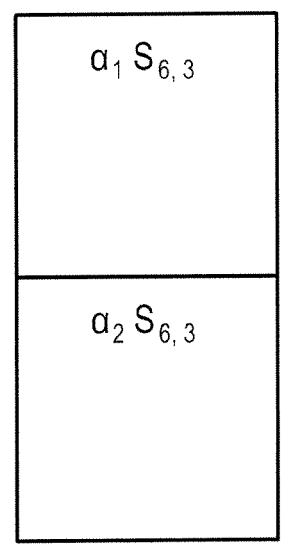

FIG. 13

ULTRASOUND AND SYSTEM FOR FORMING AN ULTRASOUND IMAGE

CROSS-REFERENCE TO RELATED APPLICATIONS

The present application claims priority from Korean Patent Application No. 10-2011-0143837 filed on Dec. 27, 2011, the entire subject matter of which is incorporated herein by reference.

TECHNICAL FIELD

The present disclosure generally relates to an ultrasound system, more particularly to an ultrasound system and a method for forming an ultrasound image by selectively extracting ultrasound data necessary for forming a target ultrasound image from the stored ultrasound data.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of target objects (e.g., human organs).

The ultrasound system may provide ultrasound images of various modes including a brightness mode image indicative of reflection coefficients of ultrasound signals (i.e., ultrasound echoes) reflected from a target object of an object with a two-dimensional image, a Doppler mode image indicative of velocities of a moving target object with spectral Doppler by using a Doppler effect, a color Doppler mode image indicative of velocities of the moving target object with colors by using the Doppler effect, an elastic image representing mechanical characteristics of tissues before and after applying compression thereto, and the like.

In particularly, the ultrasound system transmits an ultrasound signal according to the pulse repetition frequency and receives an ultrasound signal reflected from the target object (i.e., ultrasound echo), thereby forming ultrasound data to form an ultrasound image. The ultrasound data may be stored in storage. The ultrasound system may form an ultrasound image using the ultrasound data stored in the storage.

SUMMARY

The present disclosure provide an ultrasound system and a method for forming an ultrasound image by selectively extracting ultrasound data necessary for forming a target ultrasound image from the stored ultrasound data.

In one embodiment, an ultrasound system includes a storage unit configured to store ultrasound data acquired from an object; and a processor configured to selectively extract target ultrasound data necessary for forming a target ultrasound image from the ultrasound data stored in the storage unit, and to form an ultrasound image by using the extracted ultrasound data.

In another embodiment, a method of providing an ultrasound image includes a) storing ultrasound data acquired from an object; b) selectively extract ultrasound data necessary for forming a target object from the ultrasound data stored in the storage unit; and c) forming an ultrasound image by using the extracted ultrasound data.

BRIEF DESCRIPTION OF THE DRAWINGS

FIGS. 3 to 6 are schematic diagrams showing examples of transmission directions and reception directions according to one embodiment of the present disclosure.

FIG. 7 is a schematic diagram showing examples of sampling data and pixels of an ultrasound image according to one embodiment of the present disclosure.

FIGS. 8 to 11 are schematic diagrams showing examples of performing reception beam-forming according to one embodiment of the present disclosure.

FIG. 12 is a schematic diagram showing an example of setting weights according to one embodiment of the present disclosure.

FIG. 13 is a schematic diagram showing an example of setting a sampling data set according to one embodiment of the present disclosure.

DETAILED DESCRIPTION

Hereinafter, embodiments of the present disclosure will be described in detail by referring to accompanying drawings.

Figure 1:
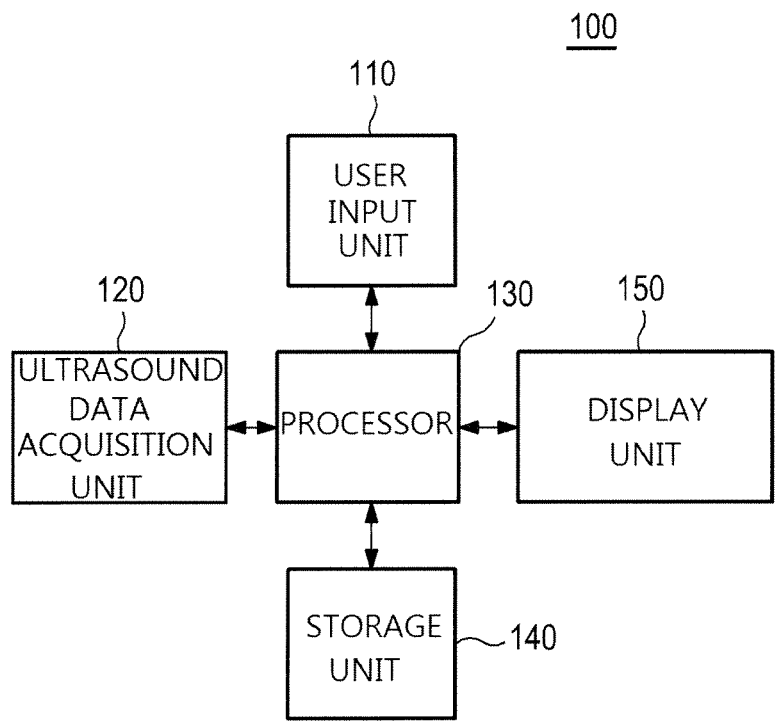
FIG. 1 is a block diagram showing an illustrative embodiment of an ultrasound system.

FIG. 1 is a block diagram showing an illustrative embodiment of an ultrasound system 100. Referring to FIG. 1, the ultrasound system 100 may include a user input unit 110.

The user input unit 110 may be configured to receive input information of a user. In one embedment, the input information may include information for setting a region of interest on a brightness mode (B-mode) image. The region of interest may include at least one of a sample volume for acquiring a Spectral Doppler image, a color box for acquiring a color Doppler image or a vector Doppler image, an M line for acquiring at least of a brightness motion (BM) mode image and a color motion (CM) mode image, and the like.

The user input unit 110 may include at least one of a control panel, a trackball, a touch screen, a mouse, a keyboard and the like.

The ultrasound system 100 may further include an ultrasound data acquisition unit 120. The ultrasound data acquisition unit 120 may be configured to transmit ultrasound signals to an object. The object may include a blood vessel, a blood flow, a heart, a liver, etc. as a target object. Further, the ultrasound data acquisition unit 120 may be configured to receive ultrasound signals reflected from the object (i.e., ultrasound echoes), thereby acquiring ultrasound data.

Figure 2:
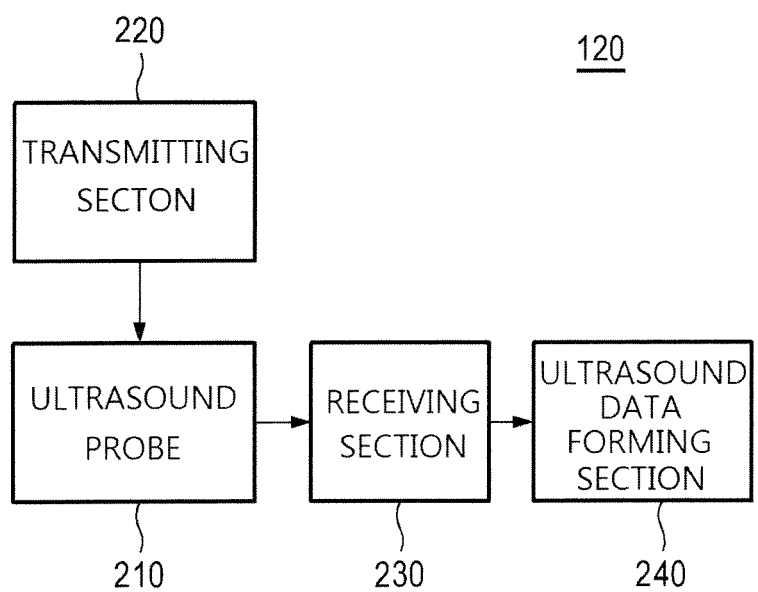
FIG. 2 is a block diagram showing an ultrasound acquisition unit according to one embodiment of the present disclosure.

FIG. 2 is a block diagram showing an illustrative embodiment of an ultrasound data acquisition unit 120. Referring to FIG. 2, the ultrasound data acquisition unit 120 may include an ultrasound probe 210.

The ultrasound probe 210 may include a plurality of transducer elements 311 (see FIG. 3), which are operable to perform reciprocal conversion between electrical signals and ultrasound signals. The ultrasound probe 210 may be configured to transmit ultrasound signals to the object and receive ultrasound signals reflected from the object (i.e., ultrasound echoes), thereby outputting electrical signals (hereinafter, referred to as receive signals). The receive signals may be analog signals. The ultrasound probe 210 may include at least one of a convex probe, a linear probe and the like.

The ultrasound data acquisition unit 120 may further include a transmitting section 220. The transmitting section 220 may be configured to control transmission of the ultrasound signals. Further, the transmitting section 220 may be configured to generate transmission pulses, which may be delivered to the respective transducer elements 311, for acquiring an ultrasound image.

In one embodiment, the transmitting section 220 may be configured to generate a first set of transmission pulses to acquire a spectral Doppler image from a region of interest based on a preset pulse repetition frequency. The ultrasound probe 210 transmits ultrasound signals to the object in response to the first set of transmission pulses. The ultrasound signals transmitted form the ultrasound probe 210 may be ultrasound signals of a plane wave, which may not be focused on a focal point, or ultrasound signals focused on a focal point. However, the ultrasound signals may not be limited thereto. The ultrasound probe 210 receives ultrasound echoes reflected from the object, thereby outputting first receive signals.

In another embodiment, the transmitting section 220 may be configured to generate a second set of transmission pulses to acquire a color Doppler image or a vector Doppler image from a region of interest based on a preset pulse repetition frequency. The ultrasound probe 210 transmits ultrasound signals to the object in response to the second set of transmission pulses. The ultrasound signals transmitted form the ultrasound probe 210 may be ultrasound signals of a plane wave, which may not be focused on a focal point, or ultrasound signals focused on a focal point. However, the ultrasound signals may not be limited thereto. The ultrasound probe 210 receives ultrasound echoes reflected from the object, thereby outputting second receive signals.

In still another embodiment, the transmitting section 220 may be configured to generate a third set of transmission pulses to acquire a BM-mode image or a CM-mode image from a region of interest based on a preset pulse repetition frequency. The ultrasound probe 210 transmits ultrasound signals to the object in response to the third set of transmission pulses. The ultrasound signals transmitted form the ultrasound probe 210 may be ultrasound signals of a plane wave, which may not be focused on a focal point, or ultrasound signals focused on a focal point. However, the ultrasound signals may not be limited thereto. The ultrasound probe 210 receives ultrasound echoes reflected from the object, thereby outputting third receive signals.

The transmitting section 220 may be further configured to generate transmission pulses (hereinafter referred to as "Doppler mode transmission pulses") corresponding to an ensemble number in consideration of the transducer elements 311 and at least one transmission direction of the ultrasound signals (i.e., transmission beam). The ultrasound probe 210 may be configured to convert the Doppler mode transmission pulses provided from the transmitting section 220 into the ultrasound signals, transmit the ultrasound signals to the object in the at least one transmission pulses, and receive the ultrasound echoes from the object to output receive signals (hereinafter referred to as "Doppler mode receive signals"). The ensemble number may represent the number of times of transmitting and receiving the ultrasound signals.

Figure 3:
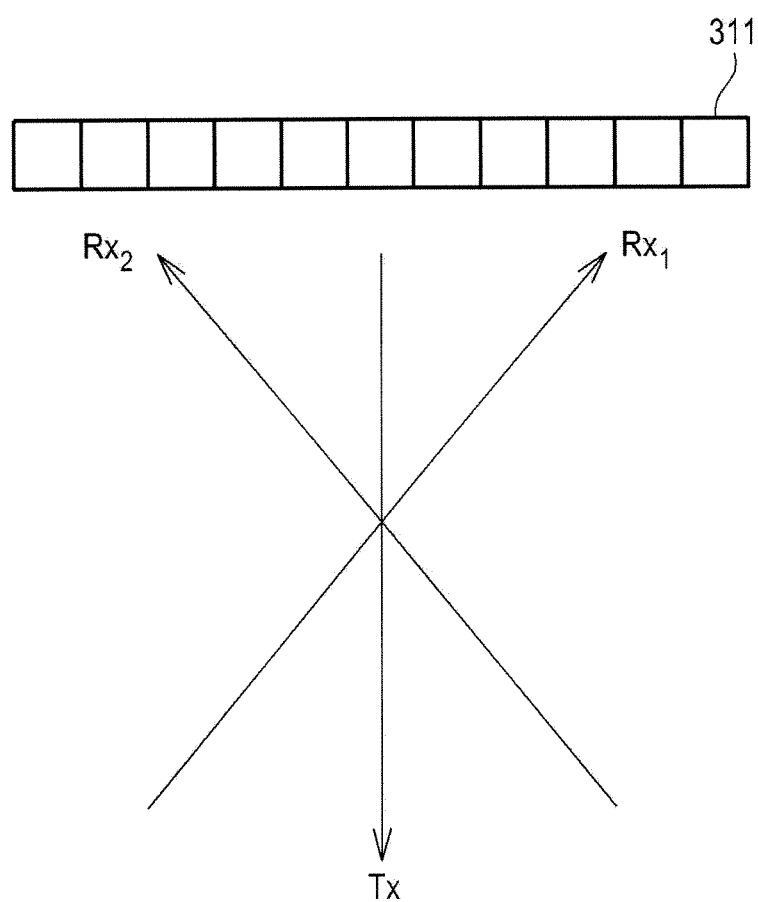

As one example, the transmitting section 220 may be configured to generate the Doppler mode transmission pulses corresponding to the ensemble number in consideration of a transmission direction Tx and the transducer elements 311, as shown in FIG. 3. The transmission direction may be one of a direction (0 degree) perpendicular to a longitudinal direction of the transducer elements 311 to a maximum steering direction of the transmission beam.

Figure 4:
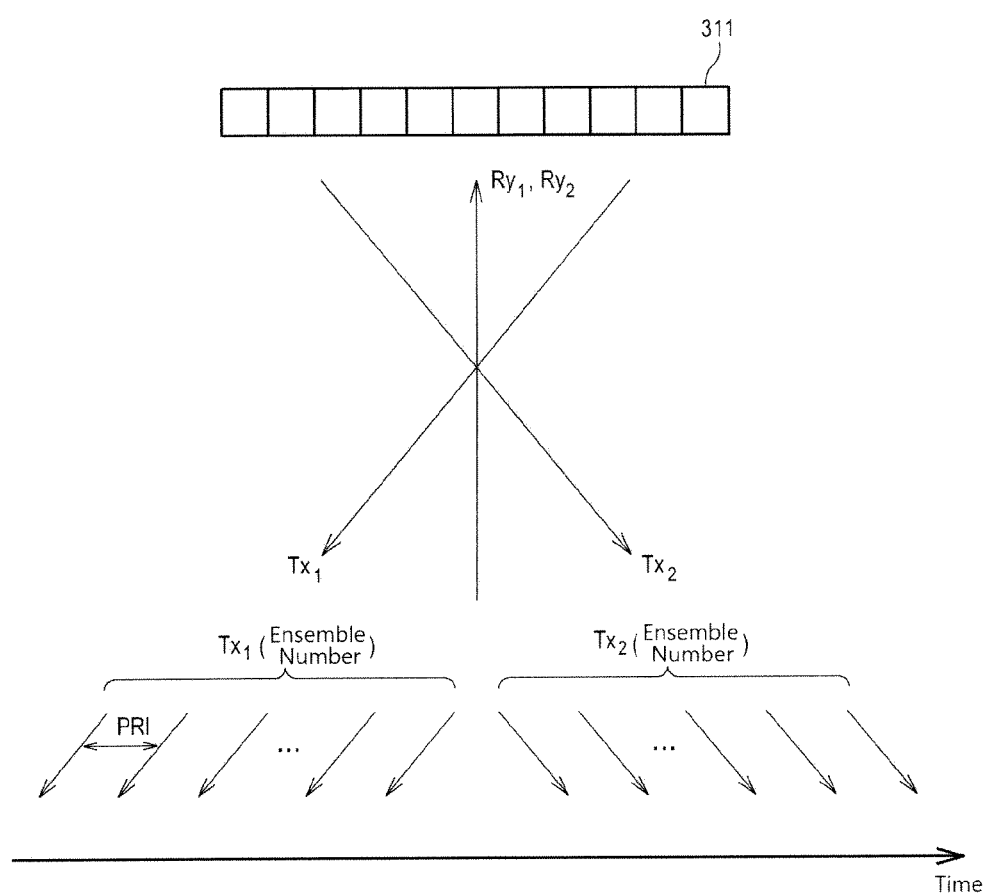

As another example, the transmitting section 220 may be configured to generate first Doppler mode transmission pulses corresponding to the ensemble number in consideration of a first transmission direction $Tx_1$ and the transducer elements 311, as shown in FIG. 4. Thus, the ultrasound probe 210 may be configured to convert the first Doppler mode transmission pulses provided from the transmitting section 220 into the ultrasound signals, transmit the ultrasound signals to the object in the first transmission direction $Tx_1$, and receive the ultrasound echoes from the object to output first Doppler mode receive signals. The transmitting section 220 may be further configured to generate second Doppler mode transmission pulses corresponding to the ensemble number in consideration of a second transmission direction $Tx_2$ and the transducer elements 311, as shown in FIG. 4. Thus, the ultrasound probe 210 may be configured to convert the second Doppler mode transmission pulses provided from the transmitting section 220 into the ultrasound signals, transmit the ultrasound signals to the object in the second transmission direction $Tx_2$, and receive the ultrasound echoes from the object to output second Doppler mode receive signals. In FIG. 4, the reference numeral PRI represents a pulse repeat interval.

In another embodiment, the transmitting section 220 may be configured to generate the B-mode transmission pulses for obtaining the B-mode image BI in consideration of the transducer elements 311. Thus, the ultrasound probe 210 may be configured to convert the B-mode transmission pulses provided from the transmitting section 220 into the ultrasound signals, transmit the ultrasound signals to the object, and receive the ultrasound echoes from the object to output the B-mode receive signals.

For example, the transmitting section 220 may be configured to generate the first Doppler mode transmission pulses in consideration of the first transmission direction $Tx_1$ and the transducer elements 311, as shown in FIG. 5. Thus, the ultrasound probe 210 may be configured to convert the first Doppler mode transmission pulses provided from the transmitting section 220 into the ultrasound signals, and transmit the ultrasound signals to the object in the first transmission direction $Tx_1$. Then, the transmitting section 220 may be further configured to generate the second Doppler mode transmission pulses in consideration of the second transmission direction $Tx_2$ and the transducer elements 311, as shown in FIG. 5. Thus, the ultrasound probe 210 may be configured to convert the second Doppler mode transmission pulses provided from the transmitting section 220 into the ultrasound signals, and transmit the ultrasound signals to the object in the second transmission direction $Tx_2$. The ultrasound probe 210 may be further configured to receive the ultrasound echoes (i.e., ultrasound echoes corresponding to first Doppler mode transmission pulses) from the object to output the first Doppler mode receive signals. The ultrasound probe 210 may be further configured to receive the ultrasound echoes (i.e., ultrasound echoes corresponding to second Doppler mode transmission pulses) from the object to output the second Doppler mode receive signals.

Thereafter, the transmitting section 220 may be configured to generate the first Doppler mode transmission pulses based on the pulse repeat interval, as shown in FIG. 5. Thus, the ultrasound probe 210 may be configured to convert the first Doppler mode transmission pulses provided from the transmitting section 220 into the ultrasound signals, and transmit the ultrasound signals to the object in the first transmission direction $Tx_1$. Thereafter, the transmitting section 220 may be further configured to generate the second Doppler mode transmission pulses based on the pulse repeat interval, as shown in FIG. 5. Accordingly, the ultrasound probe 210 may be configured to convert the second Doppler mode transmission pulses provided from the transmitting section 220 into the ultrasound signals, and transmit the ultrasound signals to the object in the second transmission direction $Tx_2$. The ultrasound probe 210 may be further configured to receive the ultrasound echoes (i.e., ultrasound echoes corresponding to first Doppler mode transmission pulses) from the object to output the first Doppler mode receive signals. Moreover, the ultrasound probe 210 may be configured to receive the ultrasound echoes (i.e., ultrasound echoes corresponding to second Doppler mode transmission pulses) from the object to output the second Doppler mode receive signals.

As described above, the transmitting section 220 may be configured to generate the first Doppler mode transmission pulses and the second Doppler mode transmission pulses corresponding to the ensemble number.

In yet another embodiment, the transmitting section 220 may be configured to generate the brightness mode transmission pulses for obtaining the brightness mode image BI in consideration of the transducer elements 311. Thus, the ultrasound probe 210 may be configured to convert the brightness mode transmission pulses provided from the transmitting section 220 into the ultrasound signals, transmit the ultrasound signals to the object, and receive the ultrasound echoes from the object to output the brightness mode receive signals.

For example, the transmitting section 220 may be configured to generate the first Doppler mode transmission pulses in consideration of the first transmission direction $Tx_1$ and the transducer elements 311 based on the pulse repeat interval, as shown in FIG. 6. Thus, the ultrasound probe 210 may be configured to convert the first Doppler mode transmission pulses provided from the transmitting section 220 into the ultrasound signals, transmit the ultrasound signals to the object in the first transmission direction $Tx_1$, and receive the ultrasound echoes from the object to output the first Doppler mode receive signals. The transmitting section 220 may be further configured to generate the second Doppler mode transmission pulses in consideration of the second transmission direction $Tx_2$ and the element 311 based on the pulse repeat interval, as shown in FIG. 6. Thus, the ultrasound probe 210 may be configured to convert the second Doppler mode transmission pulses provided from the transmitting section 220 into the ultrasound signals, transmit the ultrasound signals to the object in the second transmission direction $Tx_2$, and receive the ultrasound echoes from the object to output the second Doppler mode receive signals.

As described above, the transmitting section 220 may be configured to generate the first Doppler mode transmission pulses and the second Doppler mode transmission pulses corresponding to the ensemble number based on the pulse repeat interval.

Referring back to FIG. 2, the ultrasound data acquisition unit 120 may further include a receiving section 230. The receiving section 230 may be configured to perform analog-to-digital conversion on the receive signals provided from the ultrasound probe 210, thereby forming sampling data. Further, the receiving section 230 may be configured to perform reception beam-forming upon the sampling data in consideration of locations of the respective transducer elements to form receive-focused data. The reception beam-forming will be described in detail later.

In one embodiment, the receiving section 230 performs analog-to-digital conversion on the first receive signals, which are provided from the ultrasound probe 210, to form first sampling data. Further the receiving section 230 performs reception beam-forming upon the first sampling data to form first receive-focused signals.

In another embodiment, the receiving section 230 performs analog-to-digital conversion on the second receive signals, which are provided from the ultrasound probe 210, to form second sampling data. Further the receiving section 230 performs reception beam-forming upon the second sampling data to form first receive-focused signals.

In still another embodiment, the receiving section 230 performs analog-to-digital conversion on the third receive signals, which are provided from the ultrasound probe 210, to form third sampling data. Further the receiving section 230 performs reception beam-forming upon the third sampling data to form first receive-focused signals.

The reception beam-forming may be described with reference to the accompanying drawings.

In one embodiment, the receiving section 230 may be configured to perform the analog-digital conversion upon the receive signals provided through a plurality of channels $CH_k$, wherein $1 \leq k \leq N$, from the ultrasound probe 210 to form sampling data $S_{i,j}$, wherein the i and j are a positive integer, as shown in FIG. 7. The sampling data $S_{i,j}$ may be stored in a storage unit 140. The receiving section 230 may be further configured to detect pixels corresponding to the sampling data based on positions of the transducer elements 311 and positions (orientation) of pixels of the ultrasound image UI with respect to the transducer elements 311. That is, the receiving section 230 may select the pixels, which the respective sampling data are used as pixel data thereof, during the reception beam-forming based on the positions of the transducer elements 311 and the orientation of the respective pixels of the ultrasound image UI with respect to the transducer elements 311. The receiving section 230 may be configured to cumulatively assign the sampling data corresponding to the selected pixels as the pixel data.

Figure 8:
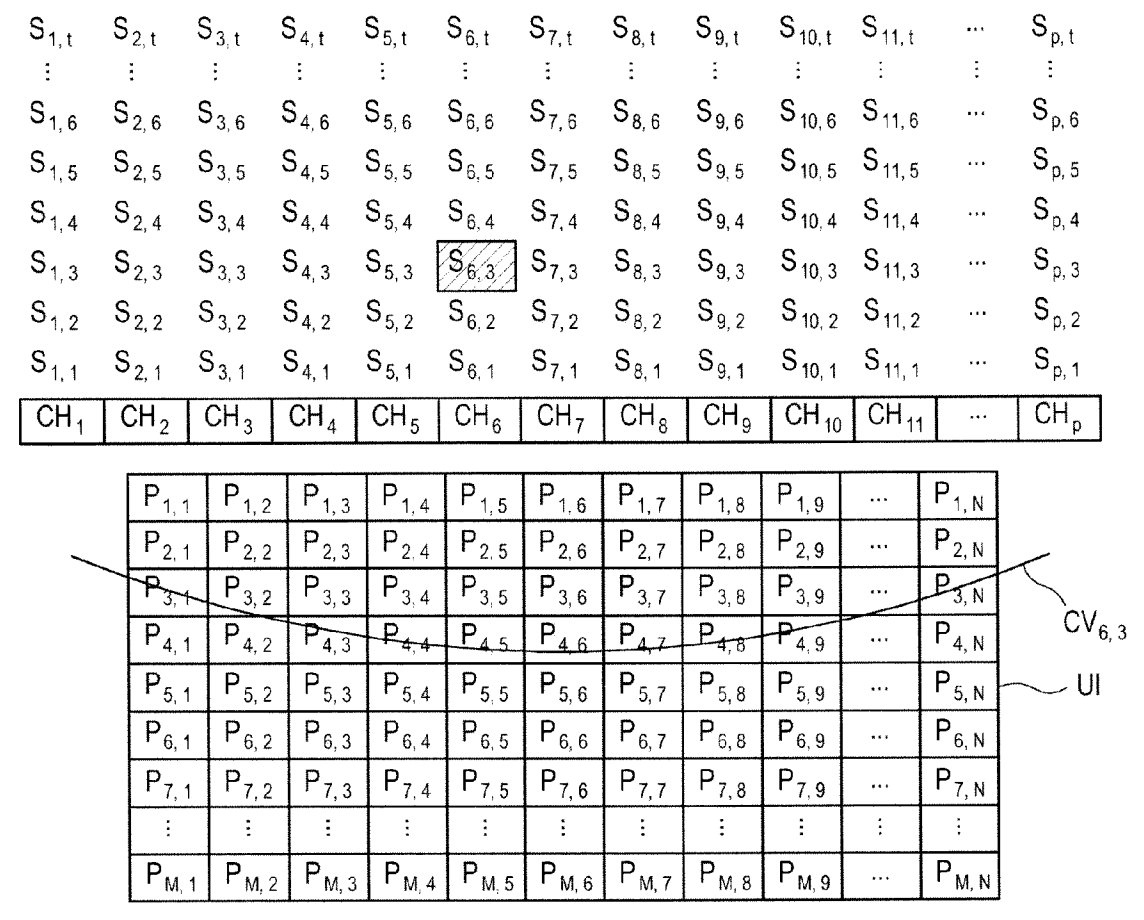
Figure 9:
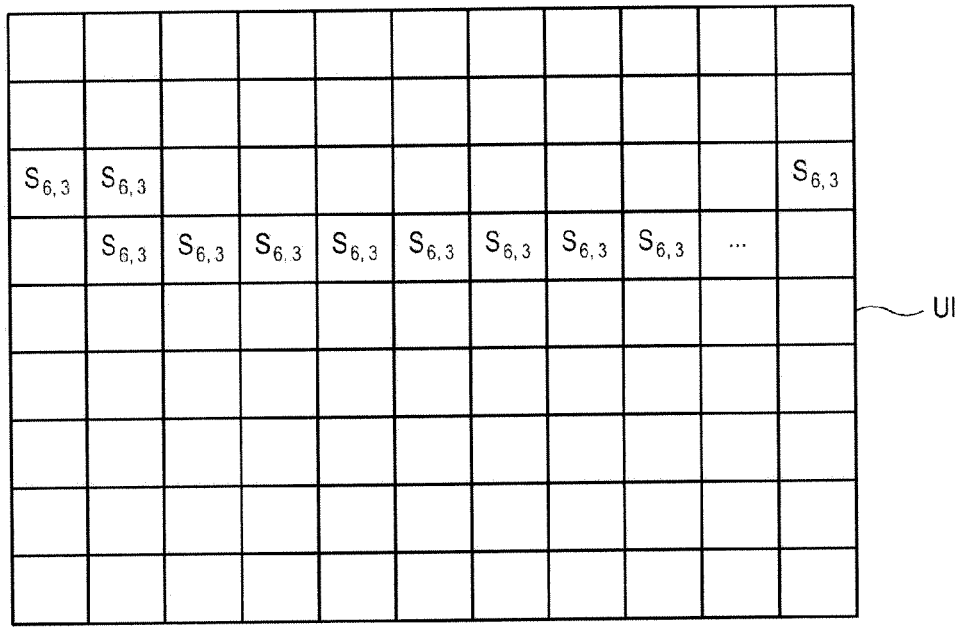

For example, the receiving section 230 may be configured to set a curve (hereinafter referred to as "reception beam-forming curve") $CV_{6,3}$ for selecting pixels, which the sampling data $S_{6,3}$ are used as the pixel data thereof, during the reception beam-forming based on the positions of the transducer elements 311 and the orientation of the respective pixels of the ultrasound image UI with respect to the transducer elements 311, as shown in FIG. 8. The receiving section 230 may be further configured to detect the pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$ corresponding to the reception beam-forming curve $CV_{6,3}$ from the pixels $P_{a,b}$ of the ultrasound image UI, wherein $1 \le a \le M$, $1 \le b \le N$. That is, the receiving section 230 may select the pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$ on which the reception beam-forming curve $CV_{6,3}$ passes among the pixels $P_{a,b}$ of the ultrasound image UI. The receiving section 230 may be also configured to assign the sampling data $S_{6,3}$ to the selected pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$, as shown in FIG. 9.

Figure 10:
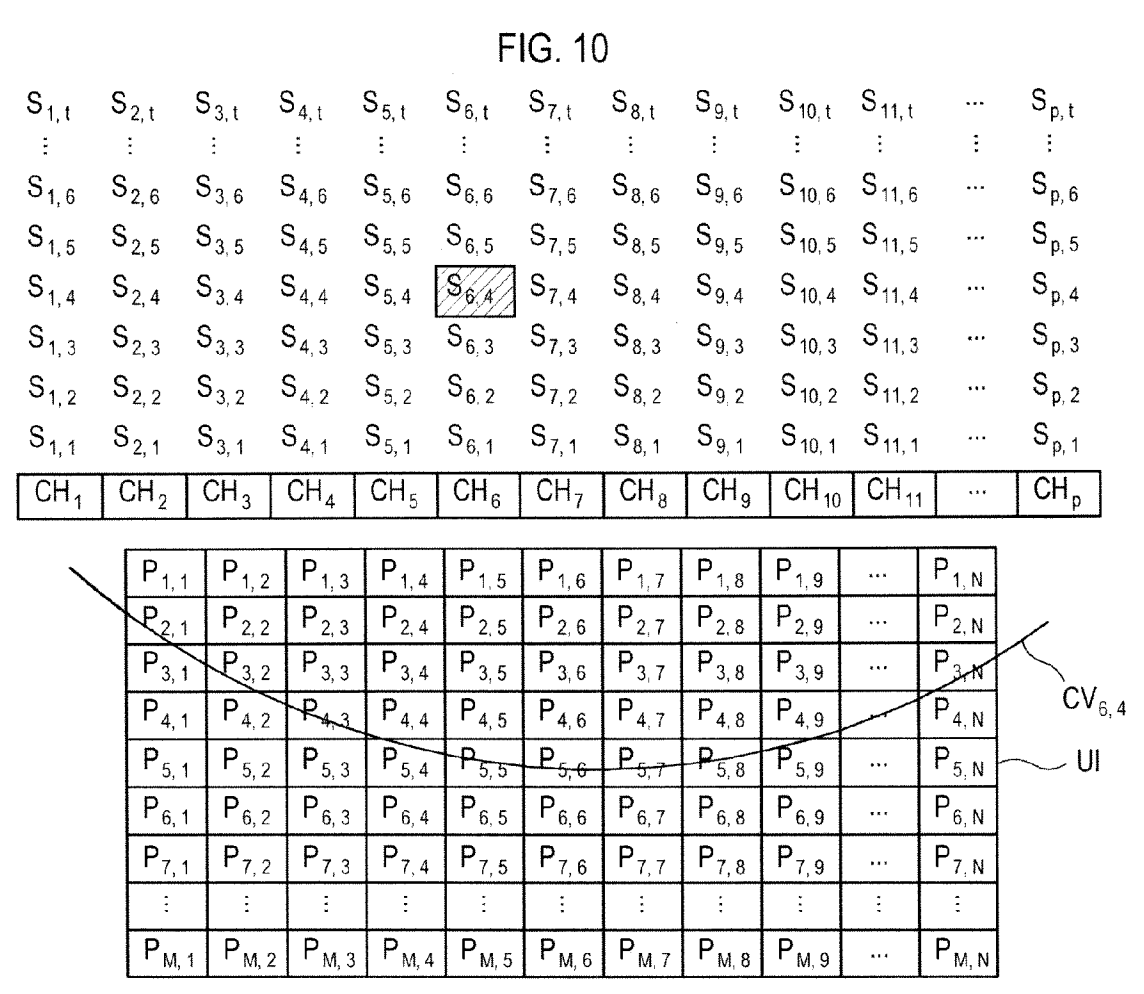

Thereafter, the receiving section 230 may be configured to set a reception beam-forming curve $CV_{6,4}$ for selecting pixels, which the sampling data $S_{6,4}$ are used as the pixel data thereof, during the reception beam-forming based on the positions of the transducer elements 311 and the orientation of the respective pixels of the ultrasound image UI with respect to the transducer elements 311, as shown in FIG. 10. The receiving section 230 may be further configured to detect the pixels $P_{2,1}, P_{3,1}, P_{3,2}, P_{4,2}, P_{4,3}, P_{4,4}, P_{5,4}, P_{5,5}, P_{5,6}, P_{5,7}, P_{5,8}, P_{4,9}, P_{5,9}, \ldots P_{4,N}, P_{3,N}$ corresponding to the reception beam-forming curve $CV_{6,4}$ from the pixels $P_{a,b}$ of the ultrasound image UI. That is, the receiving section 230 may select the pixels $P_{2,1}, P_{3,1}, P_{3,2}, P_{4,2}, P_{4,3}, P_{4,4}, P_{5,4}, P_{5,5}, P_{5,6}, P_{5,7}, P_{5,8}, P_{4,9}, P_{5,9}, \ldots P_{4,N}, P_{3,N}$ on which the reception beam-forming curve $CV_{6,4}$ passes among the pixels $P_{a,b}$ of the ultrasound image UI. The receiving section 230 may be further configured to assign the sampling data $S_{6,4}$ to the selected pixels $P_{2,1}, P_{3,1}, P_{3,2}, P_{4,2}, P_{4,3}, P_{4,4}, P_{5,4}, P_{5,5}, P_{5,6}, P_{5,7}, P_{5,8}, P_{5,9}, \ldots P_{4,N}, P_{3,N}$, as shown in FIG. 11. In this way, the respective sampling data, which are used as the pixel data, may be cumulatively assigned to the pixels as the pixel data.

The receiving section 230 may be configured to perform the reception beam-forming (i.e., summing) upon the sampling data, which are cumulatively assigned to the respective pixels $P_{a,b}$ of the ultrasound image UI to form the reception-focused data.

In another embodiment, the receiving section 230 may be configured to perform the analog-digital conversion upon the receive signals provided through the plurality of channels $CH_k$ from the ultrasound probe 210 to form the sampling data $S_{i,j}$, as shown in FIG. 7. The sampling data $S_{i,j}$ may be stored in the storage unit 140. The receiving section 230 may be further configured to detect pixels corresponding to the sampling data based on the positions of the transducer elements 311 and the position (orientation) of the pixels of the ultrasound image UI with respect to the transducer elements 311. That is, the receiving section 230 may select the pixels, which the respective sampling data are used as the pixel data thereof, during the reception beam-forming based on the positions of the transducer elements 311 and the orientation of the respective pixels of the ultrasound image UI with respect to the transducer elements 311. The receiving section 230 may be configured to cumulatively assign the sampling data corresponding to the selected pixels as the pixel data. The receiving section 230 may be further configured to determine pixels existing in the same column among the selected pixels. The receiving section 230 may be also configured to set weights corresponding to the respective determined pixels. The receiving section 230 may be additionally configured to apply the weights to the sampling data of the respective pixels.

For example, the receiving section 230 may be configured to set the reception beam-forming curve $CV_{6,3}$ for selecting pixels, which the sampling data $S_{6,3}$ are used as the pixel data thereof, during the reception beam-forming based on the positions of the transducer elements 311 and the orientation of the respective pixels of the ultrasound image UI with respect to the transducer elements 311, as shown in FIG. 8. The receiving section 230 may be further configured to detect the pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$ corresponding to the reception beam-forming curve $CV_{6,3}$ from the pixels $P_{a,b}$ of the ultrasound image UI, wherein $1 \le a \le M$, $1 \le b \le N$. That is, the receiving section 230 may select the pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$ on which the reception beam-forming curve $CV_{6,3}$ passes among the pixels $P_{a,b}$ of the ultrasound image UI. The receiving section 230 may be also configured to assign the sampling data $S_{6,3}$ to the selected pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$, as shown in FIG. 9. The receiving section 230 may be further configured to determine pixels $P_{3,2}$ and $P_{4,2}$, which exist in the same column among the selected pixels $P_{3,1}, P_{3,2}, P_{4,2}, P_{4,3}, P_{4,4}, P_{4,5}, P_{4,6}, P_{4,7}, P_{4,8}, P_{4,9}, \ldots P_{3,N}$. The receiving section 230 may be further configured to calculate a distance $W_1$ from a center of the determined pixel $P_{3,2}$ to the reception beam-forming curve $CV_{6,3}$ and a distance $W_2$ from a center of the determined pixel $P_{4,2}$ to the reception beam-forming curve $CV_{6,3}$, as shown in FIG. 12. The receiving section 230 may be additionally configured to set a first weight $\alpha_1$ corresponding to the pixel $P_{3,2}$ based on the distance $W_1$ and a second weight $\alpha_2$ corresponding to the pixel $P_{4,2}$ based on the distance $W_2$. The first weight $\alpha_1$ and the second weight $\alpha_2$ may be set to be in proportional to or in inverse proportional to the calculated distances. The receiving section 230 may be further configured to apply the first weight $\alpha_1$ to the sampling data $S_{6,3}$ assigned to the pixel $P_{3,2}$ and to apply the second weight $\alpha_2$ to the sampling data $S_{6,3}$ assigned to the pixel $P_{4,2}$. The receiving section 230 may be configured to perform the above process upon the remaining sampling data.

The receiving section 230 may be configured to perform the reception beam-forming upon the sampling data, which are cumulatively assigned to the respective pixels $P_{a,b}$ of the ultrasound image UI to form the reception-focused data.

In yet another embodiment, the receiving section 230 may be configured to perform the analog-digital conversion upon the receive signals provided through the plurality of channels $CH_k$ from the ultrasound probe 210 to form the sampling data $S_{i,j}$, as shown in FIG. 7. The sampling data may be stored in the storage unit 140. The receiving section 230 may be further configured to set a sampling data set based on the sampling data $S_{i,j}$. That is, The receiving section 230 may set the sampling data set for selecting pixels, which the sampling data $S_{i,j}$ are used as the pixel data thereof, during the reception beam-forming.

Figure 13:
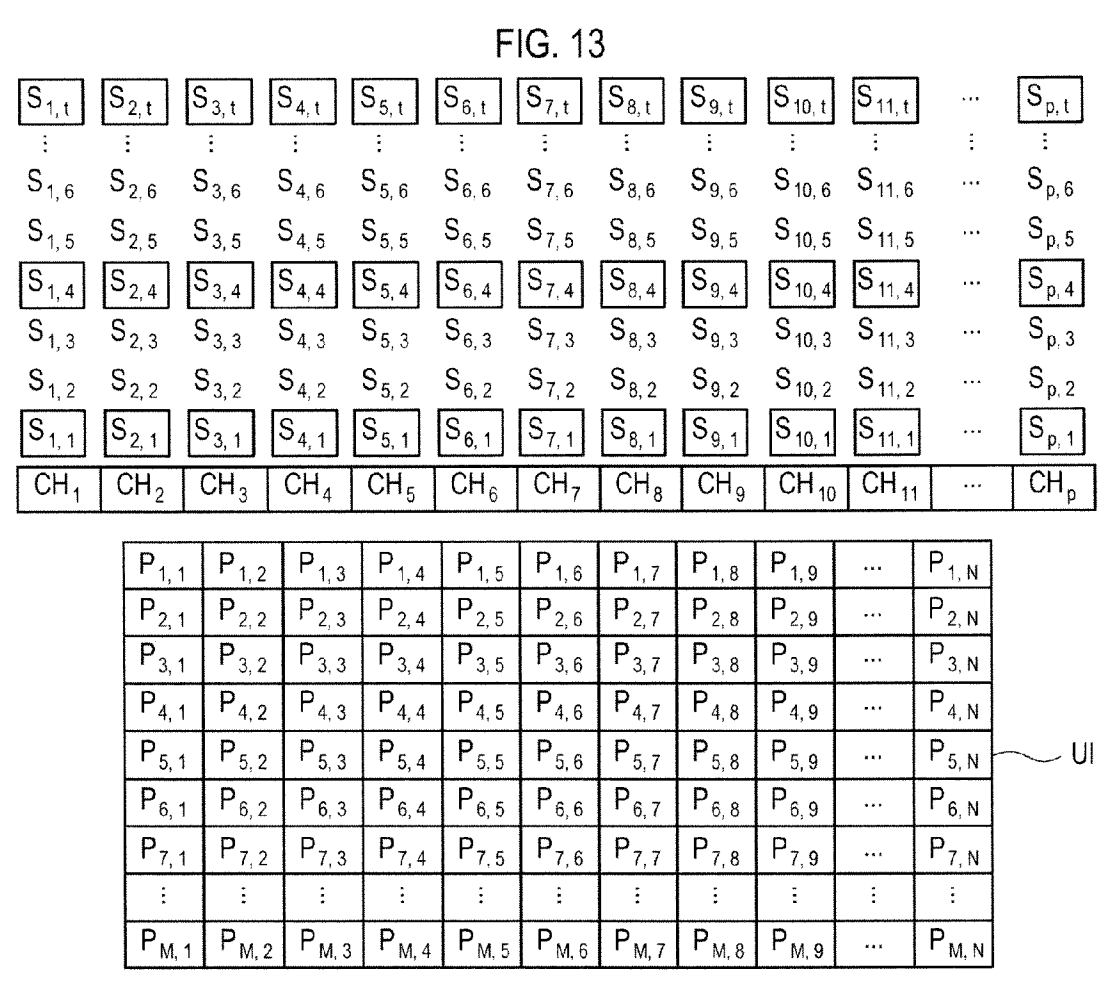

For example, the receiving section 230 may be configured to set the sampling data $S_{1,1}, S_{1,4}, \ldots S_{1,t}, S_{2,1}, S_{2,4}, \ldots S_{2,t}, S_{p,t}$ as the sampling data set (denoted by a box) for selecting the pixels, which the sampling data $S_{i,j}$ are used as the pixel data thereof, during the reception beam-forming, as shown in FIG. 13.

The receiving section 230 may be further configured to detect the pixels corresponding to the respective sampling data of the sampling data set based on the positions of the transducer elements 311 and the positions (orientation) of the respective pixels of the ultrasound image UI with respect to the transducer elements 311. That is, the receiving section 230 may select the pixels, which the respective sampling data of the sampling data set are used as the pixel data thereof, during the reception beam-forming based on the positions of the transducer elements 311 and the orientation of the respective pixels of the ultrasound image UI with respect to the transducer elements 311. The receiving section 230 may be further configured to cumulatively assign the sampling data to the selected pixels in the same manner with the above embodiments. The receiving section 230 may be also configured to perform the reception beam-forming upon the sampling data, which are cumulatively assigned to the respective pixels of the ultrasound image UI to form the reception-focused data.

In yet another embodiment, the receiving section 230 may be configured to perform a down-sampling upon the receive signals provided through the plurality of channels $CH_k$ from the ultrasound probe 210 to form down-sampling data. As described above, the receiving section 230 may be further configured to detect the pixels corresponding to the respective sampling data, based on the positions of the transducer elements 311 and the positions (orientation) of the respective pixels of the ultrasound image UI with respect to the transducer elements 311. That is, the receiving section 230 may select the pixels, which the respective sampling data are used as the pixel data thereof, during the reception beam-forming based on the positions of the transducer elements 311 and the orientation of the pixels of the ultrasound image UI with respect to the transducer elements 311. The receiving section 230 may be further configured to cumulatively assign the respective sampling data to the selected pixels in the same manner of the above embodiments. The receiving section 230 may be further configured to perform the reception beam-forming upon the sampling data, which are cumulatively assigned to the respective pixels of the ultrasound image UI to form the reception-focused data.

However, it should be noted herein that the reception beam-forming may not be limited thereto.

Referring back to FIG. 2, the ultrasound data acquisition unit 120 may further include an ultrasound data forming section 240. The ultrasound data forming section 240 may be configured to form ultrasound data for ultrasound imaging by using the receive-focused data, which are provided from the receiving section 230. Further, the ultrasound data forming section 240 may be configured to perform various data processing (e.g., gain adjustment, etc.) necessary for forming an ultrasound image upon the receive-focused data.

In one embodiment, the ultrasound data forming section 240 forms first ultrasound data for Doppler spectral imaging by using the first receive-focused data, which are provided from the receiving section 230. The first ultrasound data may include radio frequency (RF) data or in-phase/quadrature (IQ) data, but may not be limited thereto.

In another embodiment, the ultrasound data forming section 240 forms second ultrasound data for color Doppler or vector Doppler imaging by using the second receive-focused data, which are provided from the receiving section 230. The second ultrasound data may include radio frequency (RF) data or in-phase/quadrature (IQ) data, but may not be limited thereto.

In further another embodiment, the ultrasound data forming section 240 forms third ultrasound data for BM-mode or CM-mode imaging by using the third receive-focused data, which are provided from the receiving section 230. The third ultrasound data may include radio frequency (RF) data or in-phase/quadrature (IQ) data, but may not be limited thereto.

Referring back to FIG. 1, the ultrasound system 100 may further include storage unit 140. The storage may be configured to store the ultrasound data, which are acquired by the ultrasound data acquisition unit 120. In one embodiment, the storage unit 140 may be configured to store the ultrasound data for respective ultrasound images. Further, the storage unit 140 stores the input information received through the user input unit 110.

The ultrasound system 100 may further include a processor 130. The processor 130 may be coupled to the user input unit 110, the ultrasound data acquisition unit 120 and the storage unit 140. The processor 130 may include at least one of a central processing unit (CPU), a graphic processing unit (GPU), a microprocessor and the like.

Figure 14:
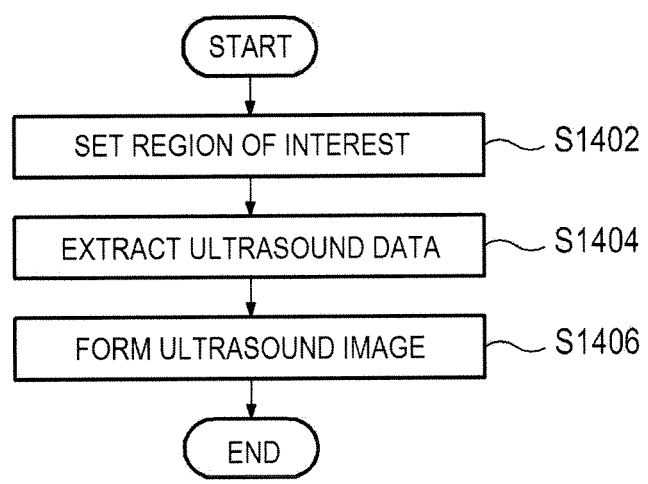
FIG. 14 is a flowchart showing a procedure of forming an ultrasound image according to one embodiment of the present disclosure.

FIG. 14 is a flowchart showing a procedure of forming an ultrasound image according to one embodiment of the present disclosure. Referring to FIG. 14, the processor 130 may be configured to set a region of interest based on the input information provided from the input unit 110 at S1402. The ultrasound data acquisition unit 120 may transmit ultrasound signals to an object and receive ultrasound echoes by considering the region of interest, thereby acquiring ultrasound data corresponding to the region of interest.

The processor 130 may be configured to retrieve the storage unit 140 to selectively extract ultrasound data necessary for forming a target ultrasound image at S1404.

In one embedment, the processor 130 is configured to set a processing pulse repetition frequency for extracting ultrasound data to be used to form a target ultrasound image based on a preset pulse repetition frequency. In such a case, the ultrasound image may include at least one of a Spectral Doppler image, a color Doppler image and a vector Doppler image. That is, the processor 130 set the processing pulse repetition frequency, which is asynchronous with (i.e., independent from) the preset pulse repetition frequency.

Figure 15:
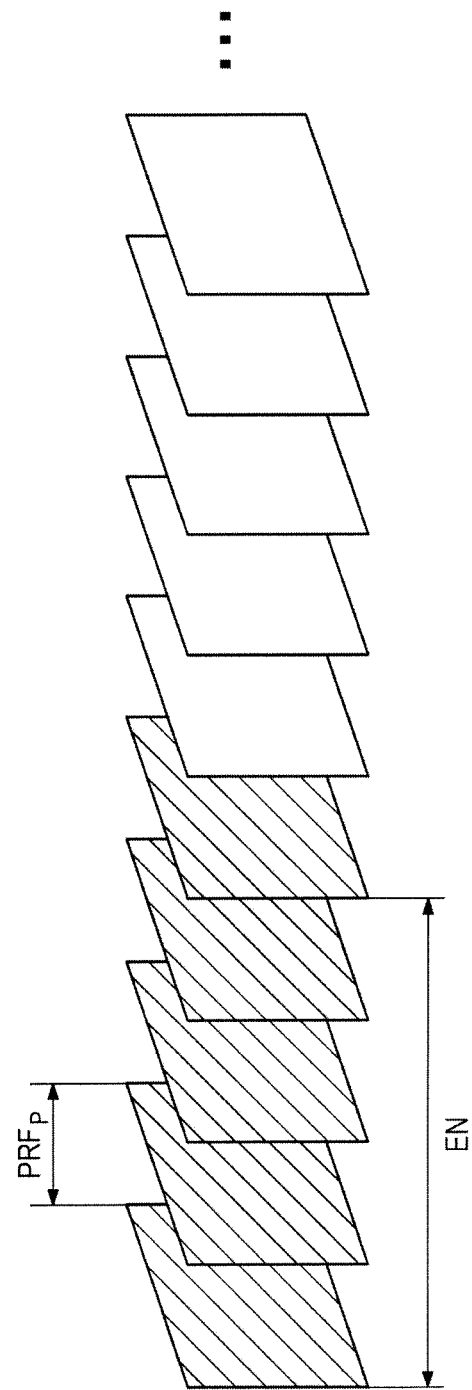
FIG. 15 is an exemplary diagram showing a pulse repetition frequency and an ensemble number according to one embodiment of the present disclosure.
Figure 16:
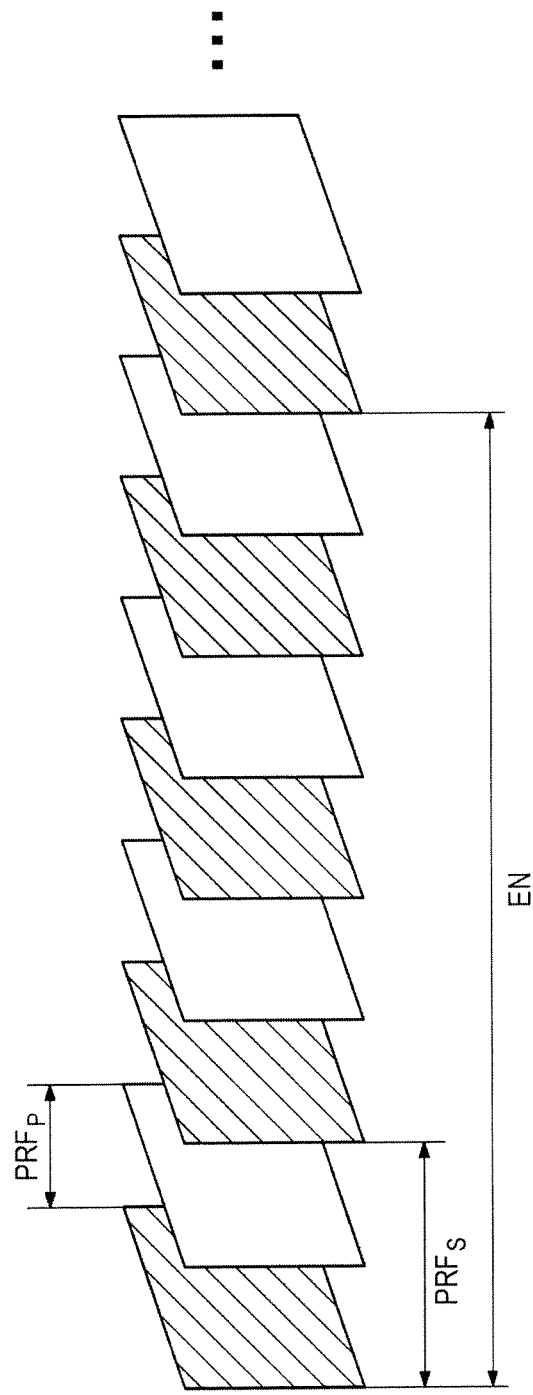
FIG. 16 is an exemplary diagram showing a repetition pulse frequency, a processing pulse repetition frequency and an ensemble number according to one embodiment of the present disclosure.

For example, the processor may set a processing pulse repetition frequency $PRF_S$, which is asynchronous with the preset pulse repetition frequency $PRF_P$ as shown in FIG. 16, based on the pulse repetition frequency $PRF_P$ as shown in FIG. 15. In FIGS. 15 and 16, a symbol EN represents an ensemble number. The processing pulse repetition frequency $PRF_S$ may be set as the following equation.

$$PRF_S = \frac{PRF_P}{N_e} \tag{1}$$

In the equation (1), Ne represents a range of ultrasound data, which may not be used to form a target ultrasound image, from the preset pulse repetition frequency as shown in FIG. 16.

That is, the processing pulse frequency $PRF_S$ may represent a pulse repetition frequency to extract ultrasound data (hatched) to be used to form a target ultrasound image by skipping ultrasound data (not hatched), which are not participated in forming the target ultrasound image, in the ultrasound data acquired in the preset pulse repetition frequency $PRF_P$, as shown in FIG. 16.

Thus, the processing pulse repetition frequency $PRF_S$ may be set to be lower than the preset pulse repetition frequency $PRF_P$, so that it may be useful to detect a velocity of blood flow, which relatively slowly flows.

In another embodiment, the processor 130 may set an ensemble number of ultrasound data to be used to form a target ultrasound image (hereinafter, referred to as a processing ensemble number). The target ultrasound image may include at least one of a Spectral Doppler image, a color Doppler image and a vector Doppler image.

Figure 17:
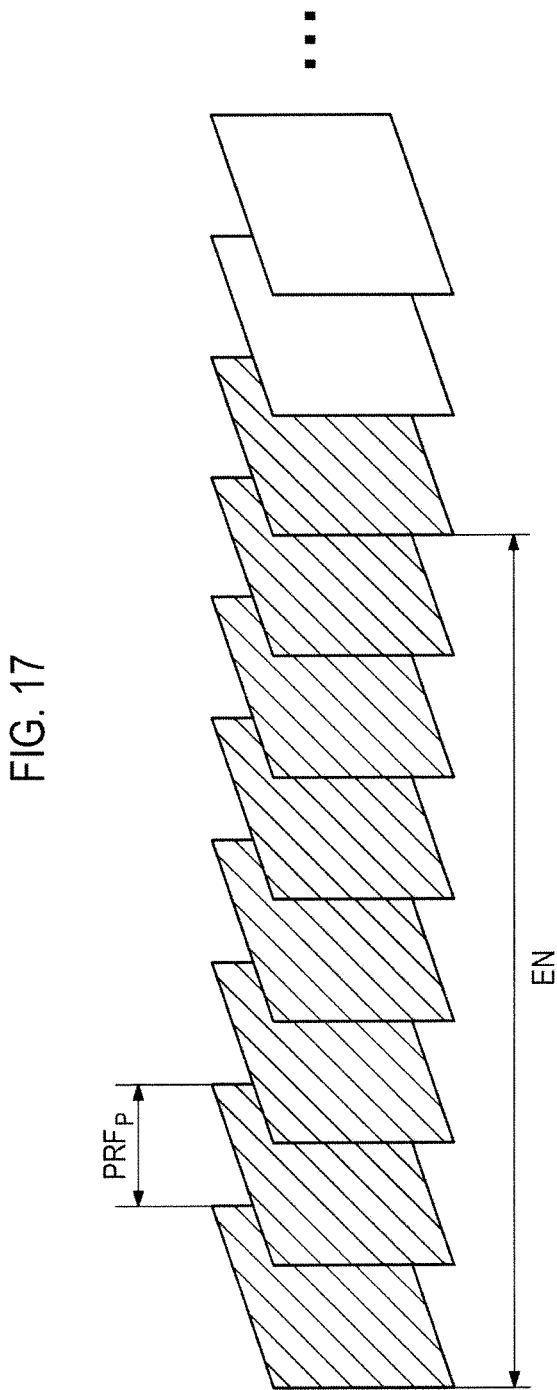
FIG. 17 is an exemplary diagram showing a pulse repetition frequency and a processing ensemble number according to one embodiment of the present disclosure.
Figure 18:
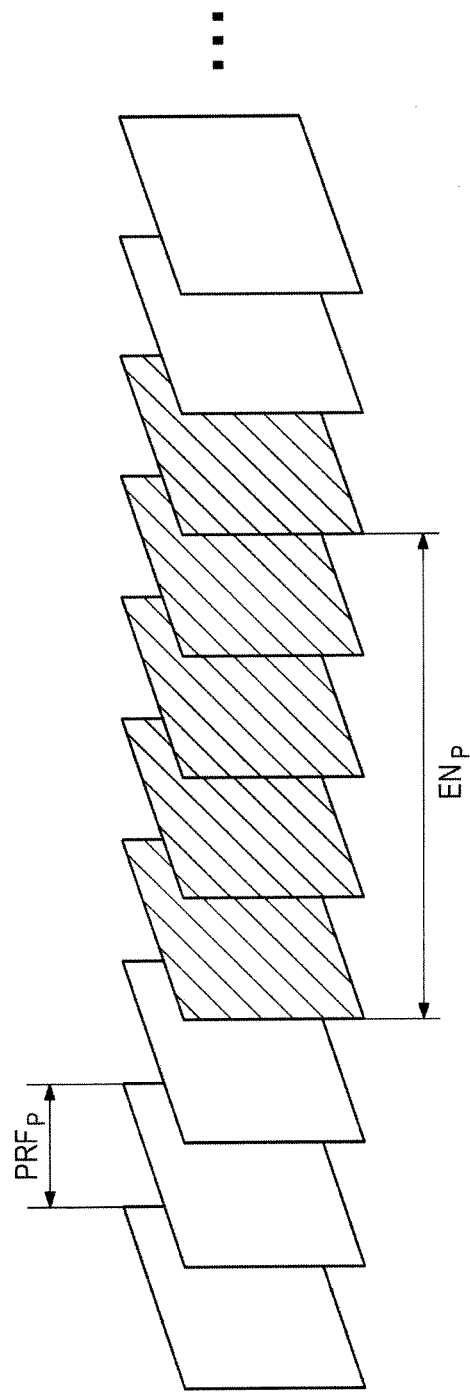
FIG. 18 is an exemplary diagram showing a pulse repetition frequency and a processing ensemble number according to another embodiment of the present disclosure.
Figure 19:
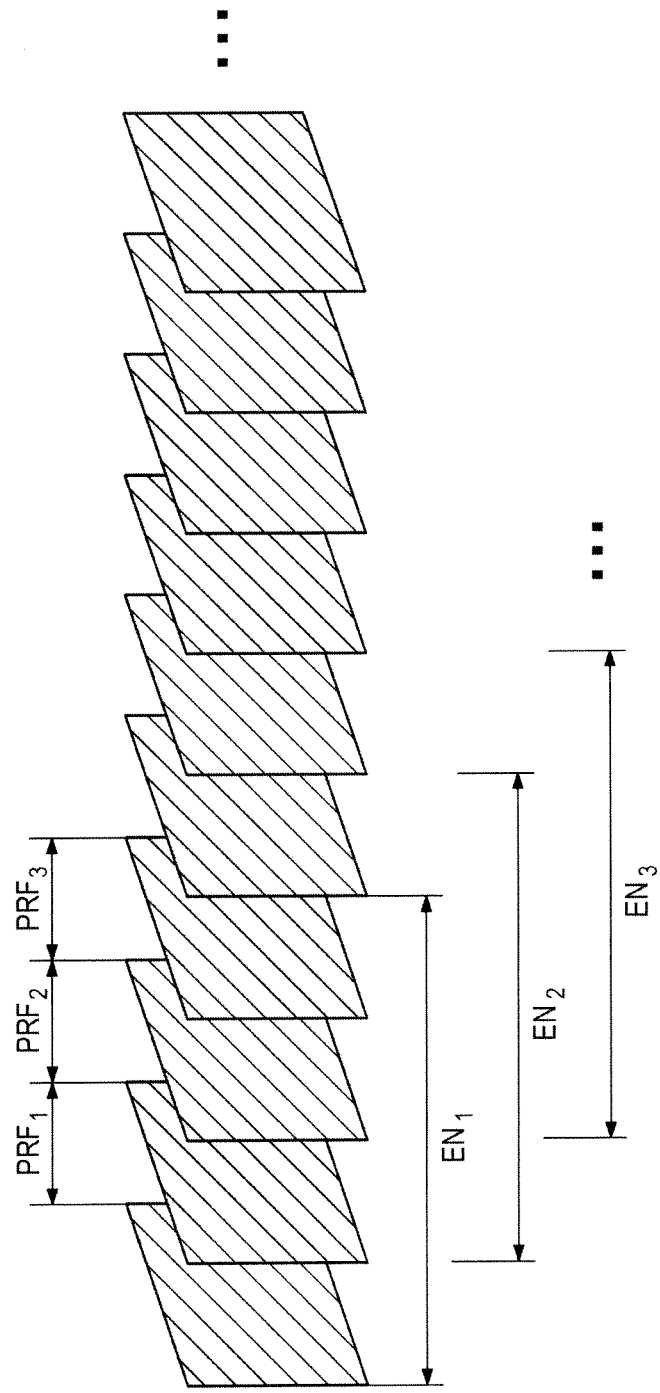
FIG. 19 is an exemplary diagram showing a pulse repetition frequency and an ensemble number according to further another embodiment of the present disclosure.

For example, when the ultrasound data corresponding to N frames are stored in the storage unit as shown in FIG. 17, the processor 130 is configured to set a range of the ultrasound data corresponding to the N frames as the processing ensemble number $EN_p$. In another embodiment, when the ultrasound data corresponding to N frames are stored in the storage unit as shown in FIG. 18, the processor 130 may be configured to set a range of the ultrasound data corresponding to i frames among the ultrasound data of the N frames stored in the storage unit 140 as the processing ensemble number $EN_p$, wherein i is a positive integer less than N.

Thus, since the processing ensemble number may be set to be greater than a predetermined ensemble number, velocities of blood flow or tissues may be more accurately detected.

Further, since the processing ensemble number may be set to be less than a predetermined ensemble number, an ultrasound image having better connectivity may be provided through a comparison with a previous ultrasound image.

In another embodiment, the processor 130 may be configured to set a range of ultrasound data corresponding to an ensemble number based on the preset pulse repetition frequency. For example, the processor 130 is configured to set a first range $EN_1$ of ultrasound data corresponding to an ensemble number with respect to a first preset pulse repetition frequency $PRF_1$, set a second range $EN_2$ of ultrasound data corresponding to an ensemble number with respect to a second preset pulse repetition frequency $PRF_2$, and set a third range $EN_3$ of ultrasound data corresponding to an ensemble number with respect to a third preset pulse repetition frequency $PRF_3$.

Since the ultrasound data corresponding to the ensemble number may be extracted per each preset pulse repetition frequency, velocities of blood flow or tissues, which are moved during a maximum pulse repetition frequency, may be indicative as an ultrasound image.

In another embodiment, the processor 130 may be configured to set a range of ultrasound data to form an ultrasound image, i.e., sweep speed. The sweep speed may be set through the well-known method, so that detailed description thereof will be omitted herein. The ultrasound image may include at least one of a BM-mode image and a CM-mode image. Further, the processor 130 may be configured to set a plurality of sweep speeds.

Referring to FIG. 14 again, the processor 130 may be configured to form an ultrasound image by using the extracted ultrasound data at S1406.

For example, the processor 130 may be configured to form Doppler signals by using the extracted ultrasound data. The processor 130 may form a Spectral Doppler image corresponding to the sample volume (i.e., region of interest) by using the Doppler signals.

In another embodiment, the processor 130 may be configured to form Doppler signals by using the extracted ultrasound data. The processor 130 may form a color Doppler image corresponding to the sample volume (i.e., color box) by using the Doppler signals.

In further another embodiment, the processor 130 may be configured to form vector information by using the extracted ultrasound data. That is, the processor 130 may form vector information corresponding to motion (i.e., velocities and directions) of the target object by using the extracted ultrasound data.

Generally, when the transmission direction of the ultrasound signals is equal to the reception direction of the ultrasound echoes and a Doppler angle is 0, the following relationship may be established:

$$X\cos\theta = \frac{C_0 f_d}{2 f_0} \quad (2)$$

In equation (2), X represents a reflector velocity (i.e., velocity of target object), $C_0$ represents a sound speed in the object, $f_d$ represents a Doppler shift frequency, and $f_0$ represents an ultrasound frequency.

The Doppler shift frequency $f_d$ may be calculated by the difference between a frequency of the ultrasound signals (i.e., transmission beam) and a frequency of the ultrasound echoes (i.e., reception beam). Also, the velocity component $X \cos \theta$ projected to the transmission direction may be calculated by the equation 1.

When the transmission direction of the ultrasound signals (i.e., transmission beam) is different to the reception direction of the ultrasound echoes (i.e., reception beam), the following relationship may be established:

$$X\cos\theta_T + X\cos\theta_R = \frac{C_0 f_d}{f_0} \quad (3)$$

In equation 3, $\theta_T$ represents an angle between the ultrasound signals (i.e., transmission beam) and the blood flow, and $\theta_R$ represents an angle between the ultrasound echoes (i.e., reception beam) and the blood flow.

Figure 20:
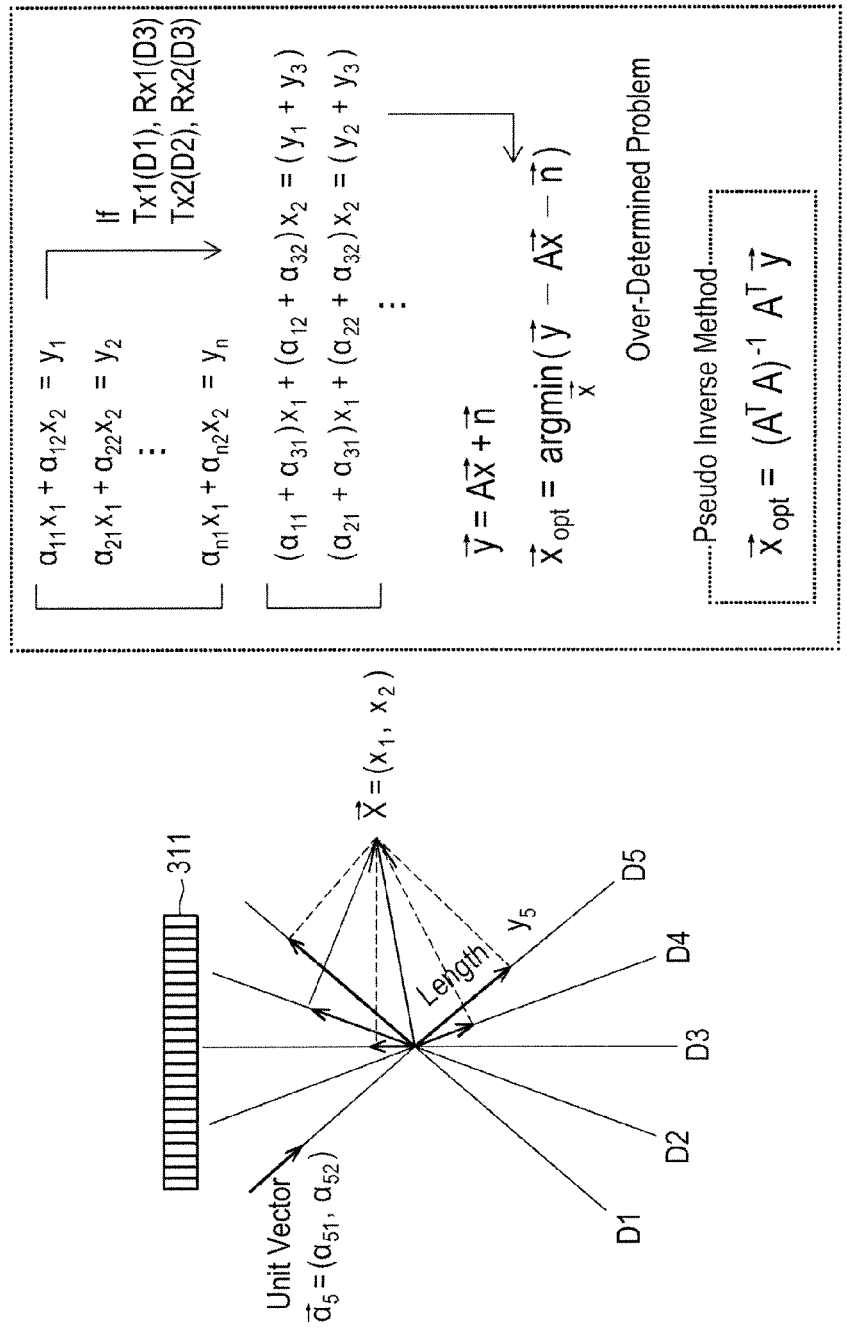
FIG. 20 is a schematic diagram showing an example of the transmission directions, the reception directions, the vector information and an over-determined problem.

FIG. 20 is a schematic diagram showing an example of the transmission directions, the reception directions, the vector information and an over-determined problem. Referring to FIG. 16, when the ultrasound signals (i.e., transmission beam) are transmitted in a first direction D1 and the ultrasound echoes (i.e., reception beam) are received in the first direction D1, the following relationship may be established:

$$\vec{\alpha}_1 \vec{X} = \alpha_{11} x_1 + \alpha_{12} x_2 = y_1 = X \cos \theta \quad (4)$$

In equation 3, $\vec{\alpha}_1 = (\alpha_{11}, \alpha_{12})$ represents a unit vector of the first direction D1, $\vec{X} = (x_1, x_2)$ represents variables, and $y_1$ is calculated by equation 1.

When the ultrasound signals (i.e., transmission beam) are transmitted in a second direction D2 and the ultrasound echoes (i.e., reception beam) are received in a third direction D3, the following relationship may be established:

$$(\alpha_{21}+\alpha_{31})x_1+(\alpha_{22}+\alpha_{32})x_2=(y_2+y_3)=X\cos\theta_2+X\cos\theta_3 \quad (5)$$

Equations 4 and 5 assume a two-dimensional environment. However, equations 4 and 5 may be expanded to a three-dimensional environment. That is, when expanding equations 3 and 4 to the three-dimensional environment, the following relationship may be established:

$$\alpha_{11}x_1+\alpha_{12}x_2+\alpha_{13}x_3=y$$

$$(\alpha_{31}+\alpha_{21})x_1+(\alpha_{32}+\alpha_{22})x_2=(y_3+y_2) \quad (6)$$

In the case of the two-dimensional environment (i.e., two-dimensional vector), at least two equations are required to calculate the variables $x_1$ and $x_2$. For example, when the ultrasound signals (i.e., transmission beam) are transmitted in the third direction D3 and the ultrasound echoes (i.e., reception beam) are received in the second direction D2 and a fourth direction D4 as shown in FIG. 16, the following equations may be established:

$$(\alpha_{31}+\alpha_{21})x_1+(\alpha_{32}+\alpha_{22})x_2=(y_3+y_2) \qquad (7)$$

The vector $\vec{X}=(x_1, x_2)$ may be calculated by the equations of equation 6.

When the reception beam-forming is performed in at least two angles (i.e., at least two reception directions), at least two equations may be obtained and represented as the over-determined problem, as shown in FIG. 16. The over-determined problem is well known in the art. Thus, it has not been described in detail so as not to unnecessarily obscure the present disclosure. The over-determined problem may be solved by a pseudo inverse method, a weighted least square method and the like based on noise characteristics added to the Doppler shift frequency. That is, M×N equations may be obtained by M transmission directions and the reception beam-forming of N reception directions at every transmission.

In another embodiment, the processor 130 may be configured to form at least one of a BM-mode image and a CM-mode image corresponding to a region of interest (i.e., M line) by using the extracted ultrasound data. The BM-mode image and the CM-mode image may be formed through the various well-known methods, so that detained description thereof will be omitted herein.

Referring to FIG. 1 again, the ultrasound system 100 may further include a display unit 150. The display unit may be configured to display an ultrasound image formed by the processor 130. Further, the display unit 150 may be configured to display a B-mode image.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound probe configured to transmit ultrasound signals to an object based on a first ensemble number and receive ultrasound echoes reflected from the object:
   a storage configured to store a plurality of radio frequency (RF) data sets acquired based on the ultrasound echoes from the object; and
   a processor configured to set a second ensemble number different from the first ensemble number, selectively extract a subset of the plurality of RF data sets necessary for forming a target ultrasound image from the plurality of RF data sets stored in the storage based on the second ensemble number, and form the target ultrasound image by using the extracted subset of the plurality of RF data sets.

2. The ultrasound system of claim 1, wherein the target ultrasound image includes at least one of a spectral Doppler image, a color Doppler image and a vector Doppler image.

3. The ultrasound system of claim 1, wherein the processor is configured to:
   set a processing pulse repetition frequency to extract the subset of the plurality of RF data sets necessary for forming the target ultrasound image, and
   extract the subset of the plurality of RF data sets from the storage based on the processing pulse repetition frequency.

4. The ultrasound system of claim 3, wherein the ultrasound probe transmits ultrasound signals to the object based on a preset pulse repetition frequency, and the processing pulse repetition frequency is asynchronous with the preset pulse repetition frequency.

5. The ultrasound system of claim 4, wherein the processor is configured to set the processing pulse frequency to extract the subset of the plurality of RF data sets to be used to form of the target ultrasound image by skipping ultrasound data, which are not participated in forming the target ultrasound image, in the ultrasound data storage.

6. The ultrasound system of claim 1, wherein the target ultrasound image includes at least one of a brightness motion mode image and a color motion mode image.

7. The ultrasound system of claim 6, wherein the processor is configured to extract the subset of the plurality of RF data sets necessary for forming the target ultrasound image from the stored ultrasound data by using a sweep speed.

8. The ultrasound system of claim 1, wherein the ultrasound signals include ultrasound signals of a plane wave or focused signals.

9. A method of forming an ultrasound image, comprising:
   transmitting ultrasound signals to an object based on a first ensemble number and receiving ultrasound echoes reflected from the object;
   storing, in storage, a plurality of radio frequency (RF) data sets based on the ultrasound echoes acquired from the object;
   setting a second ensemble number different from the first ensemble number;
   selectively extracting, from among the stored plurality of RF data sets, a subset of the plurality of RF data sets necessary for forming a target ultrasound image; and
   forming the target ultrasound image by using the extracted subset of the plurality of RF data sets.

10. The method of claim 9, wherein the target ultrasound image includes at least one of a Spectral Doppler image, a color Doppler image and a vector Doppler image.

11. The method of claim 10, wherein the selectively extracting includes:
    setting a processing pulse repetition frequency to extract the subset of the plurality of RF data sets necessary for forming the target ultrasound image, and
    extracting the subset of the plurality of RF data sets from the storage based on the processing pulse repetition frequency.

12. The method of claim 11, wherein the selectively extracting includes setting the processing pulse frequency to extract the subset of the plurality of RF data sets to be used to form the target ultrasound image by skipping ultrasound data, which are not participated in forming the target ultrasound image, in the storage.

13. The method of claim 10, wherein transmitting ultrasound signals includes transmitting ultrasound signals to the object based on a preset pulse repetition frequency, and the processing pulse repetition frequency is asynchronous with the preset pulse repetition frequency.

14. The method of claim 9, wherein the target ultrasound image includes at least one of a brightness motion mode image and a color motion mode image.

15. The method of claim 14, wherein the selectively extracting includes extracting the subset of the plurality of RF data sets necessary for forming the target ultrasound image by using a sweep speed.

16. The method of claim 9, wherein the ultrasound signals include ultrasound signals of a plane wave or focused signals.

* * * * *